(12) United States Patent
Kim

(10) Patent No.: US 11,519,922 B2
(45) Date of Patent: Dec. 6, 2022

(54) METHODS FOR IDENTIFYING RISK OF CHEMOTHERAPY-INDUCED CARDIOTOXICITY AND TARGETED MEDICAL INTERVENTION

(71) Applicant: Hyesook Kim, Bloomfield Hills, MI (US)

(72) Inventor: Hyesook Kim, Bloomfield Hills, MI (US)

(73) Assignee: Detroit R&D, Inc., Bloomfield Hills, MI (US)

( * ) Notice: Subject to any disclaimer, the term of this patent is extended or adjusted under 35 U.S.C. 154(b) by 269 days.

(21) Appl. No.: 16/259,499

(22) Filed: Jan. 28, 2019

(65) Prior Publication Data

US 2020/0241019 A1 Jul. 30, 2020
US 2022/0276265 A9 Sep. 1, 2022

Related U.S. Application Data

(60) Provisional application No. 62/623,775, filed on Jan. 30, 2018.

(51) Int. Cl.
*G01N 33/92* (2006.01)
*G01N 33/68* (2006.01)
*G01N 33/573* (2006.01)

(52) U.S. Cl.
CPC .......... *G01N 33/92* (2013.01); *G01N 33/573* (2013.01); *G01N 33/6887* (2013.01); *G01N 2405/00* (2013.01); *G01N 2560/00* (2013.01); *G01N 2800/32* (2013.01); *G01N 2800/42* (2013.01); *G01N 2800/50* (2013.01); *G01N 2800/52* (2013.01)

(58) Field of Classification Search
CPC .......... G01N 2405/00; G01N 2560/00; G01N 2800/32; G01N 2800/42; G01N 2800/50; G01N 2800/52; G01N 33/573; G01N 33/6887; G01N 33/92
See application file for complete search history.

(56) References Cited

U.S. PATENT DOCUMENTS 6,534,282 B2 3/2003 Kim et al.
7,695,927 B2 * 4/2010 Kim ................... G01N 33/88
435/7.72

OTHER PUBLICATIONS

Stevens et al., "Cardiotoxicity due to Chemotherapy: the Role of Biomarkers," Curr. Cardiol. Rep., 2015, 17:49, pp. 1-8.*
Zordoky et al., "Acute doxorubicin cardiotoxicity alters cardiac cytochrome P450 expression and arachidonic acid metabolism in rats," Toxicol. Appl. Pharmacol., 2010, vol. 242, pp. 38-46.*
Sharkey et al., "Differential cardiotoxicity in response to chronic doxorubicin treatment in male spontaneous hypertension-heart failure (SHHF), spontaneously hypertensive (SHR), and Wistar Kyoto (WKY) rats," Toxicol. Appl. Pharmacol., 2013, vol. 273, issue 1, pp. 47-57.*
CDC, the National Center for Health Statistics (NCHS): Underlying cause of death 1999-2013 on CDC Wonder Online Database, 2014, p. 1.
Fryar et al., Prevalence of uncontrolled risk factors for cardiovascular diseases: United States, 1999-2010. NCHS Data Brief., 2012, vol. 103, pp. 1-8.
Lotrionte et al., Review and meta-analysis of incidence and clinical predictors of anthracycline cardiotoxicity. Am. J. Cardiol. 2013, vol. 112, pp. 1980-1984.
United Cancer Support Foundation, Breast cancer statistics in United States, Oct. 20, 2018. Education, pp. 1-3.
Ky et al., Early increases in multiple biomarkers predict subsequent cardiotoxicity in patients with breast cancer treated with doxorubicin, taxanes, and trastuzumab. J. Am. Coll Cardiol. 2014, vol. 8, pp. 809-816.
Stevens et al., Cardiotoxicity due to Chemotherapy: The Role of Biomarkers. Curr. Cardiol. Rep. 2015, vol. 17, 49, pp. 1-8.
Seidman et al., Cardiac dysfunction in the trastuzumab clinical trials experience. J. Clin. Oncol. 2002 vol. 5, pp. 1215-1221.
Yang et al., The role of 14,15-dihydroxyeicosatrienoic acid levels in inflammation and its relationship to lipoproteins. Lipids Health. Dis. 2013, vol. 23, 151, pp. 1-7.
Santos et al., The role of soluble epoxide hydrolase in preeclampsia. Med. Hypotheses 2017, vol. 108, pp. 81-85.
Cha et al., Quantitative analysis of H5N1 DNA hybridization on nanowell array electrode. J. Nanosci. Nanotechnol. 2013, vol. 13, pp. 5245-5249.
Lee et al., Wafer-scale nanowell array patterning based electrochemical impedimetric immunosensor. J. Biotechnol. 2013, vol. 168, pp. 584-588.
Reagan et al., Comparison of cardiac troponin I and T, including the evaluation of an ultrasensitive assay, as indicators of doxorubicin-induced cardiotoxicity Toxicol. Pathol 2013, vol. 41, pp. 1146-1158.

* cited by examiner

*Primary Examiner* — Galina M. Yakovleva

(57) ABSTRACT

This invention discloses diagnosis of risk of chemotherapy-induced cardiotoxicity by measurement of increased expression of soluble epoxide hydrolase in vitro and in vivo in cells, tissues or animals including measurement of increased levels of soluble epoxide hydrolase metabolites, e.g., 14,15-DHET and 11,12-DHET, in biological fluids. This invention also includes diagnosis of risk of chemotherapy-induced cardiotoxicity by measuring increased levels of oxidative stress in cells, tissues or animals including measurement of increased levels of oxidative stress biomarkers, e.g., 8-isoprostane, in biological fluids. Fatty acid and protein biomarkers to diagnose the risk of chemotherapy-induced cardiotoxicity are detected using various detection methods including mass spectrometry and immunoassay such as ELISA, Western blot analysis or label-free microwell and nanowell technologies. This invention discloses targeted medical intervention for a subject who is at risk or with chemotherapy-induced cardiotoxicity by treating with soluble epoxide hydrolase inhibitor(s) with or without antioxidants to prevent or ameliorate the chemotherapy-induced cardiotoxicity.

4 Claims, 7 Drawing Sheets

A. sEH: DOX-induced protein

B. NAG-1: Plasma cardiotoxicity biomarker

A. Quantitation of 14,15-DHET levels using a standard

B. Quantitation of TnI levels using a standard

METHODS FOR IDENTIFYING RISK OF CHEMOTHERAPY-INDUCED CARDIOTOXICITY AND TARGETED MEDICAL INTERVENTION

GOVERNMENT SUPPORT

Research in this application was supported, in part, by a Phase I SBIR Contract from the National Heart, Lung, and Blood Institute (NHLBI Contract HHSN261201600028C).

BACKGROUND OF THE INVENTION

1. Technical Field

This invention relates to methods to identify risk of chemotherapy-induced cardiotoxicity using biomarkers. The method includes diagnosis of risk of chemotherapy-induced cardiotoxicity by measuring increased levels of expression of soluble epoxide hydrolase in vitro and in vivo including cells, tissues or animals. The method includes diagnosis of risk of chemotherapy-induced cardiotoxicity by measuring increased levels of activity of soluble epoxide hydrolase including 14,15-DHET or 11,12-DHET in biological fluids. The method also includes diagnosis of risk of chemotherapy-induced cardiotoxicity by measuring increased levels of oxidative stress in vitro and in vivo including cells, tissues or animals. The method also includes diagnosis of risk of chemotherapy-induced cardiotoxicity by measuring increased levels of oxidative stress using 8-isoprostane levels in biological fluids. Fatty acid and protein biomarkers to diagnose risk of chemotherapy-induced cardiotoxicity are determined using various detection methods including mass spectrometry, Western blot analysis, ELISA or label-free microwell and nanowell technologies. This invention includes treatment using soluble epoxide hydrolase inhibitor with or without antioxidants to prevent or ameliorate chemotherapy-induced cardiotoxicity.

2. Background Art

Center for Disease Control and Prevention (CDC), the National Center for Health Statistics (NCHS) reported that during 1999-2013, 1 of every 4 deaths in the United States (0.6 million people/year) was a result of coronary heart disease (CHD) (1), which is predicted to increase each year (2).

Chemotherapy treatment of cancer patients without surgery and before and after surgery has become a routine treatment for cancer. Many successful chemotherapy agents which inhibit cell proliferation and/or metastasis have increased the 5-year survival rate of cancer patients. However, the chemotherapeutic agents are toxic to heart tissue and linked to heart failure. An anthracycline a DNA/RNA intercalator, doxorubicin (Adriamycin), daunorubicin, epirubicin or idarubicin in combination with paclitaxel (Taxol) (microtubule binder) is used to treat many cancers including breast, ovarian and lung cancers. Anthracycline chemotherapy efficiently treats various cancers. However, it has cardiotoxic effects which lead to heart failure (6%) and subclinical heart disease (18%) (3).

Over 3.1 million women in the US in 2017 were subjected to breast cancer chemotherapy (4). Treatment with DOX for 3 months followed by one-year treatment with trastuzumab for HER2-positive breast cancer patients is associated with cardiac dysfunction including symptomatic heart failure (HF) (18%) (5).

Chemotherapy-induced cardiotoxicity leads to heart failure, symptomatic left ventricular dysfunction (LVD) and reduced left ventricular ejection fraction (LVEF). The 2D-echocardiography widely used for diagnosis of CHD including heart failure and LVD is not suitable for early detection of cardiotoxicity (6). A few drawbacks of the 2D-echocardiography are high screening cost, need for a skilled technician and detection of cardiotoxicity only when the damage is occurred to the extent that recovery opportunity of heart function, LVD or LVEF, is not available (6).

Anthracycline and/or trastuzumab-associated cardiotoxicity is defined as either a cardiomyopathy with a reduction of LVEF ≥5% to <55% with symptoms of heart failure or an asymptomatic reduction of LVEF ≥10% to <55% by the Cardiac Review and Evaluation Committee (CREC) (7).

Early diagnosis (prediction) of chemotherapy-induced cardiotoxicity may offer a targeted (precision) drug treatment opportunity for patients.

Epoxyeicosatrienoic acids (EETs) are primary cardioprotective metabolites formed by cytochrome P450 (CYP) 2C/2J. Soluble epoxide hydrolase (sEH) rapidly metabolizes EETs to dihydroxyeicosatrienoic acids (DHETs) causing hypertension (8,10).

Blood and urinary 14,15-DHET is a biomarker of sEH-induced hypertension and cardiovascular disease in rats and humans (8-10). The sEH biomarker in human was validated in a blind test using human urine specimens obtained from hypertensive (preeclamptic) and normotensive patients (10).

An electrochemical nano-biosensor detects a change in electrical signal due to hybridization of a target molecule with a capture molecule, i.e., a fatty acid, a protein, a DNA or an RNA biomarker in serum, which binds to an antibody or a complementary DNA probe coated on a gold-surfaced nanowell (11,12).

SUMMARY OF INVENTION

The present invention provides methods to identify risk of chemotherapy-induced cardiotoxicity using biomarkers. This invention includes diagnosis of risk of chemotherapy-induced cardiotoxicity by measuring increased levels of expression of soluble epoxide hydrolase in vitro and in vivo including cells, tissues or animals. The method includes diagnosis of risk or presence of chemotherapy-induced cardiotoxicity by measuring increased levels of activity of soluble epoxide hydrolase including 14,15-DHET in biological fluids. This invention also includes diagnosis of risk of chemotherapy-induced cardiotoxicity by measuring increased levels of oxidative stress in vitro and in vivo including cells, tissues or animals. The method also includes diagnosis of risk of chemotherapy-induced cardiotoxicity by measuring increased levels of oxidative stress using 8-isoprostane levels in biological fluids. Fatty acid and protein biomarkers to diagnosis risk of chemotherapy-induced cardiotoxicity are detected using various methods including mass spectrometry, Western blot analysis, ELISA or label-free microwell and nanowell technologies. This invention discloses targeted medical intervention of the subject who has risk or presence of chemotherapy-induced cardiotoxicity by treating with soluble epoxide hydrolase inhibitor(s) with or without antioxidants to prevent or ameliorate the chemotherapy-induced cardiotoxicity.

DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Chemo and radiation therapy are the most common treatments given to cancer patients. However, this treatment may induce cardiac events such as hypertension, left ventricular dysfunction, cardiomyopathy and heart failure.

Acute cardiotoxicity from anthracyclines, e.g., doxorubicin (DOX), occurs as early as 6 months after completion of 3 months anthracycline treatment and chronic cardiotoxicity from anthracyclines occurs in ~2-5% of patients ~1 year after completion of chemotherapy. Detection of early biomarkers, which predict cardiac dysfunction before any damage occurs, offers an opportunity to adjust an individual's dosage and protocol during chemo and radiation therapy and provide targeted medical intervention.

The present invention provides methods to identify risk and/or presence of chemotherapy- and radiation therapy-induced cardiotoxicity by measuring increased levels of expression or activity of soluble epoxide hydrolase in vitro and in vivo including cells, tissues or animals and related cell media and biological fluids using various detection methods including Western blot analysis, ELISA and label-free microwell and nanowell technologies.

Soluble epoxide hydrolase (sEH) rapidly metabolizes EETs to DHETs causing hypertension (8,10) and cardiovascular diseases (9). To find whether anthracycline treatment, which induce cardiovascular diseases, increases sEH activity in heart cells, H9c2 rat cardiomyocytes were incubated for 2 hr with media with and without 1 µM DOX (FIG. 1 and FIG. 2).

Figures 1A, 1B:
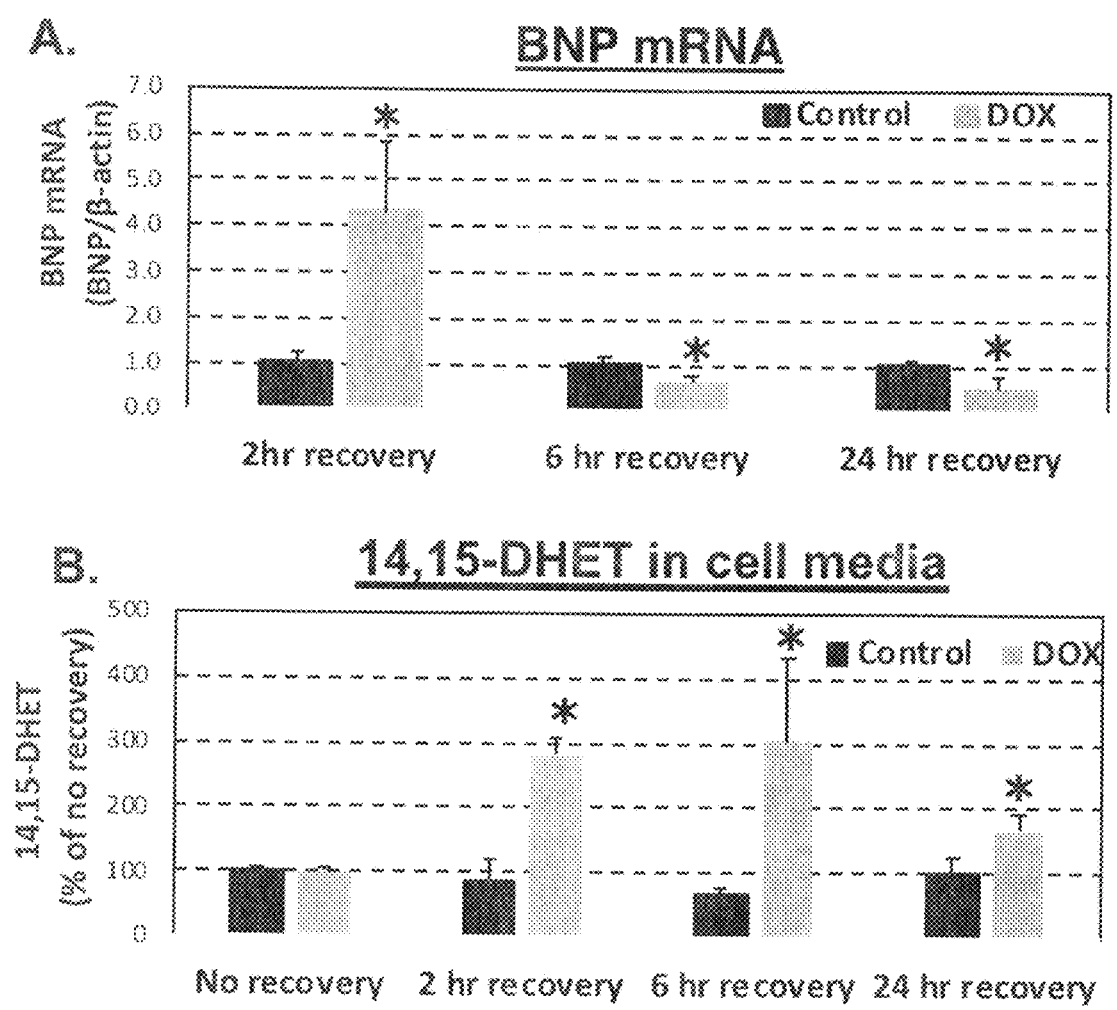
FIGS. 1A and 1B show the effect of doxorubicin (DOX) on H9c2 rat cardiomyocytes. Cells were treated for 2 hr with media containing 1 µM DOX, washed and kept for 2, 6 and 24 hr in media without DOX. BNP mRNA levels in H9c2 cells were assessed by qRT-PCR (A) and cell media was collected and extracted with ethyl acetate for 14,15-DHET analyses using ELISA kit (Detroit R&D) (B). *p<0.05.
Figure 2:
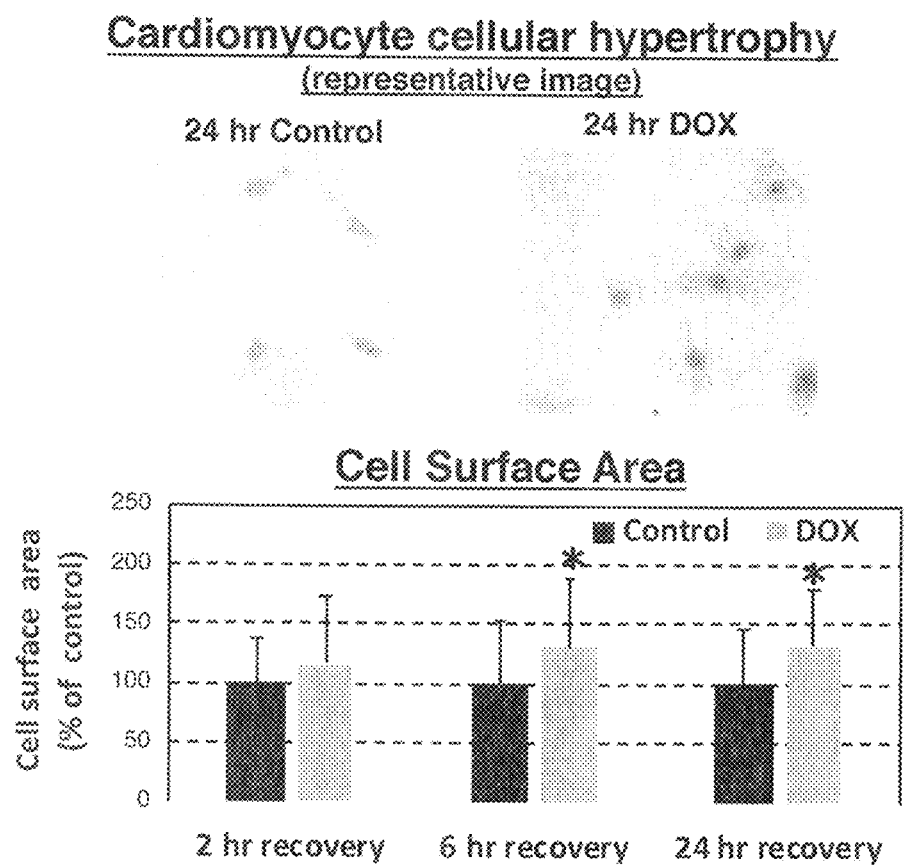
FIG. 2 shows the effect of doxorubicin (DOX) on H9c2 rat cardiomyocyte surface area as a measurement of cellular hypertrophy. Cells were treated for 2 hr with media containing 1 µM DOX, washed and kept for 2, 6 and 24 hr in media without DOX. Cell sizes (cell surface area) were measured using image J software. Results expressed as mean±SD (n=6-44)

Cells and media were collected after 2, 6 and 26 hr recovery periods (FIG. 1 and FIG. 2, Recovery).

Cell viability was determined using the 3-[4,5-dimethylthiazol-2-yl]-2,5-diphenyltetrazolium bromide (MTT) assay (13) for cells incubated with and without 1 µM of DOX in media for 2 hr followed by fresh media for another 24 hours. The DOX treated cells maintained more than 90% cell viability compared to untreated control cells.

Increased cell surface area (hypertrophy) was found at 6 hr and 24 hr after DOX treatment (p<0.05) whereas no changes were observed after 2 hr (~100 cells measured/group) (FIG. 2).

Brain natriuretic peptide (BNP) mRNA levels of the control and treated cells were measured by reverse-transcription/real time PCR (Sybr green) as previously described (13). Results were normalized using β-actin mRNA levels obtained by reverse-transcription/real time PCR (Sybr green) (13). Normalized BNP levels were decreased 6 hr and 24 hr after 2 hr of DOX treatment (p<0.05) (FIG. 1A) when cardiomyocyte hypertrophy occurred (FIG. 1A). This result demonstrated that decreased BNP mRNA levels are a biomarker of anthracycline-induced cardiotoxicity.

It was surprising that the effect of DOX treatment induced an almost 4-fold increase of BNP mRNA at 2 hr of recovery of the DOX treatment (FIG. 1A) when no change in cell size was detected (FIG. 2). This result suggested that 2 hr recovery is the best time point to find biomarkers that precede the incidence of cardiomyocyte hypertrophy.

Figures 3A, 3B, 3C, 3D:
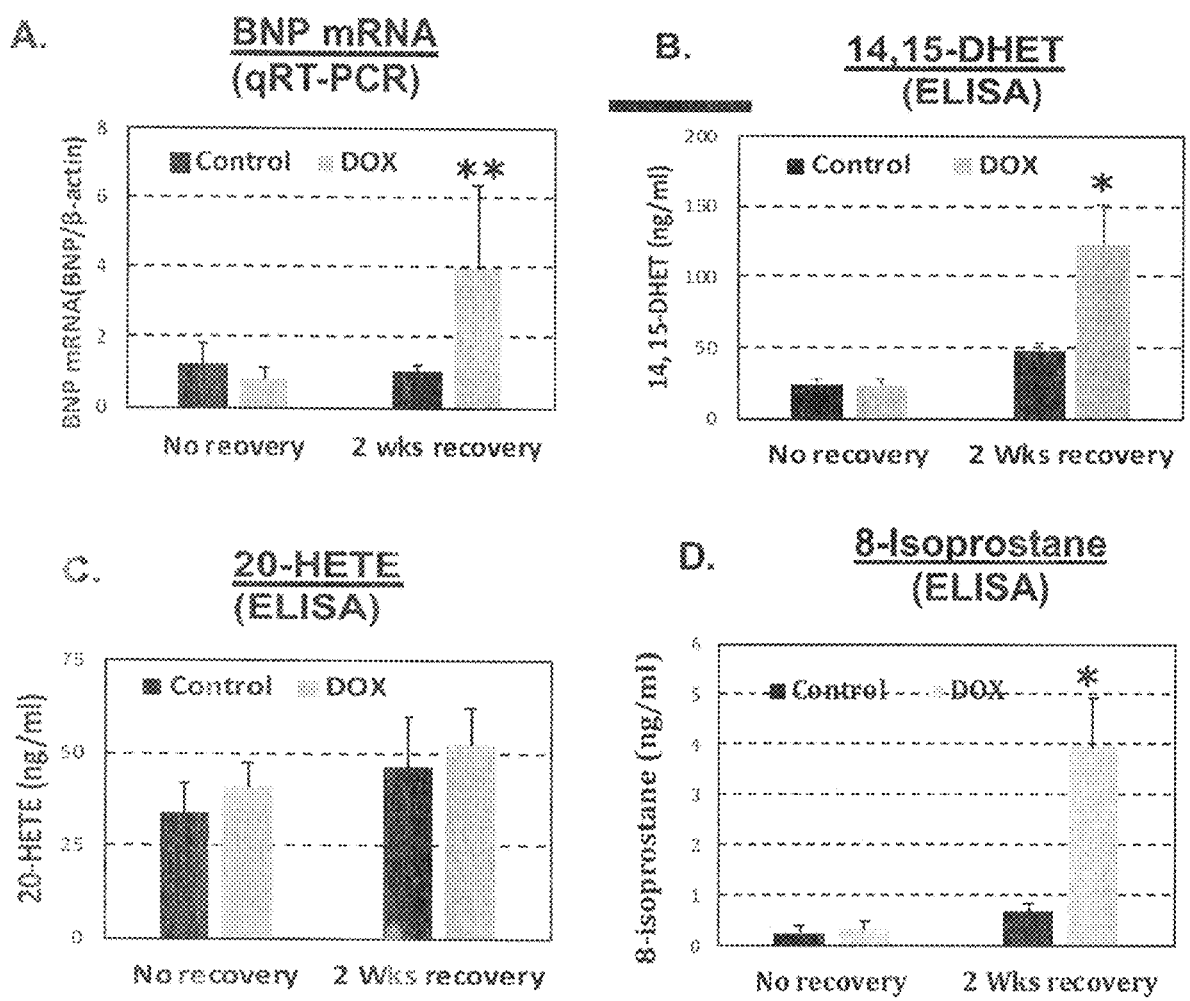
FIGS. 3A through 3D show the effect of doxorubicin (DOX) treatment on BNP mRNA and serum 14,15-DHET and 20-HETE levels in rat. Rats were euthanized at 48 hr (no recovery) or after 2 weeks (2 weeks recovery) following injection of the rats for 2 weeks with saline (control) or DOX (3 mg/kg/week). BNP mRNA levels in heart were assessed by qRT-PCR and results were normalized by β-actin mRNA (A). Levels of 14,15-DHET (B), 20-HETE (C) and 8-isoprostane (D) were assessed after extraction of fatty acids with ethyl acetate using ELISA kit (Detroit R&D). Results expressed as mean±SD (n=4-6). *p<0.05 and **p<0.01.

An approximately 4-fold increase of BNP mRNA levels in heart tissues without cardiotoxicity was also detected in a female rat study (FIG. 3A).

These results strongly suggested that increased BNP levels after DOX treatment are an early biomarker for DOX-induced cardiotoxicity.

H9c2 cardiomyocytes were treated for 2 hr with and without 1 µM DOX. Levels of 14,15-DHET in cell media increased ~3-fold ($p<0.05$) after a 2 hr recovery period prior to detection of cellular hypertrophy at 6 hr and 24 hr recovery periods. Levels of 14,15-DHET, a primary metabolite of cytosolic sEH remained elevated after 6 and 24 hr of recovery periods ($p<0.05$) (FIG. 1B).

This result demonstrated that sEH expression increased at an early stage when no cellular hypertrophy occurred (FIG. 1B). Thus, measurement of the sEH activity predicts cardiomyocyte damage in advance and any biomarkers of increased sEH activity, e.g., 14,15-DHET and 11,12-DHET, are early biomarkers for anthracycline-induced cardiotoxicity.

Expression of sEH enzyme in the cells was confirmed by detection of increased 14,15-DHET formation activity after 1 µM EET (substrate) treatment.

Figure 5A:
FIGS. 5A and 5B show the effect of doxorubicin (DOX) on soluble epoxide hydrolase (sEH) expression in rat H9c2 cardiomyocytes cells (A) and NAG-1 (MIC-1, GDF-15), a plasma cardiotoxicity biomarker (B). Panel A, cells harvested at 6 hr with (Lane 2) and without (Lane 1) treatment of doxorubicin (DOX) (2 hr, final concentration 1 µM). Protein expression of sEH, GAPDH and beta-actin expressed in the cells were assessed by Western blot analysis. Expression levels of sEH were normalized by beta-actin protein levels and Panel B, Western blot analysis carried out under non-reducing/non-denaturing condition for NAG-1 protein in plasma samples obtained from healthy subjects (pooled plasma sample, control) and 3 breast cancer patients with cardiovascular disease (cardiotoxicity, Innovative Research)

Increased sEH protein levels after DOX treatment was detected by Western blot analysis using sEH antibody (Detroit R&D) (FIG. 5A).

Increased 14,15-DHET level in biological fluids, e.g., blood and urine, is a biomarker for hypertension and cardiovascular diseases. Our cell study demonstrated that metabolites of sEH, e.g., 14,15-DHET, detected in biological fluids are early biomarkers of cardiotoxicity and the sEH enzyme is a target enzyme to prevent occurrence of cardiotoxicity by treating the patient with an sEH inhibitor.

The cell study also demonstrated that metabolites of sEH, e.g., 14,15-DHET, detected in biological fluids are biomarkers of sEH-dependent cardiotoxicity for the patient whose heart tissues are damaged or heart function is decreased after anthracycline treatment and the sEH-dependent diseases can be treated with an sEH inhibitor.

A study on serum biomarkers to detect risk of chemotherapy-induced cardiotoxicity was carried out using female rats treated with and without DOX (3 mg/kg/week, i.v. for 2 weeks) (no recovery group: Control and DOX, n=6/group) and with a 2-week recovery period (2 weeks recovery group: Control and DOX, n=6/group).

Decreased BNP mRNA levels are indicative of heart cell damage (FIG. 1 and FIG. 2). As proven by the increased BNP mRNA levels in the rat heart tissues (FIG. 3A), histochemical analysis of the heart tissues revealed no vacuolization or heart tissue damage occurred after a 2-week recovery period.

BNP mRNA levels in heart tissues were measured by reverse-transcription/real time PCR (Sybr green) and normalized using β-actin mRNA levels (13). After 2 weeks of recovery following DOX treatment (no heart tissue damage), BNP mRNA levels in heart tissue increased ~4-fold compared to the levels in control tissue ($p<0.01$) (FIG. 3A), verifying the cardiomyocytes study which revealed ~4-fold increase of BNP mRNA levels after 2 hr recovery when no hypertrophy occurred ($p<0.05$) (FIG. 1A). When cellular hypertrophy occurred at 6 hr and 24 hr recovery, the BNP mRNA levels were lower than control ($p<0.05$) (FIG. 1A). Decreased BNP mRNA levels in cardiomyocytes is a biomarker of cellular hypertrophy.

As in the rat cardiomyocyte study (FIG. 1 and FIG. 2), BNP mRNA levels in rat heart tissues increased prior to cardiac hypertrophy. These results demonstrated that the increased BNP level is an early biomarker for anthracycline-induced cardiotoxicity.

To verify that 14,15-DHET levels can be used as an early biomarker for prediction of DOX-dependent cardiotoxicity as previously found in the rat cardiomyocyte study (FIG. 1 and FIG. 2), levels of 14,15-DHET (sEH metabolite) in serum samples from control and DOX-treated rats with and without 2-week recovery were measured using a 14,15-DHET ELISA kit (Detroit R&D).

Levels of 20-HETE (CYP4A/4F-dependent hypertension biomarker) and 8-isoprostane (non-enzymatic oxidative stress biomarker) in rat serum samples were also measured using 20-HETE and 8-isoprostane ELISA kits, respectively, from Detroit R&D.

The 14,15-DHET, 20-HETE and 8-isoprostane ELISA results showed that all three biologically active fatty acids did not significantly change after two weeks (3 mg/kg body weight/week) of DOX treatment (no recovery) (FIGS. 3. B, C and D, respectively).

However, two weeks after the second DOX injection (2 weeks recovery), when cardiotoxicity was not detected, levels of 14,15-DHET and 8-isoprostane were increased compared to the control group (FIGS. 3. B and D, respectively). No changes in levels of 20-HETE in rat serum samples between the two groups were observed after DOX treatment with and without 2-week recovery (FIG. 3C).

These results demonstrated that 14,15-DHET and 8-isoprostane are early biomarkers which predict DOX-induced cardiotoxicity. Inhibition of the sEH activity will ameliorate DOX-induced cardiotoxicity.

The 14,15-DHET and 8-isoprostane biomarkers are detected in various biological fluids including blood and urine and an elevated level of 14,15-DHET is a blood and urinary biomarker of hypertension and cardiovascular disease (CVD) (8-10).

Biomarkers which predict anthracycline-caused cardiotoxicity in rat serum and heart tissue samples are summarized in Table 1.

Figure 4:
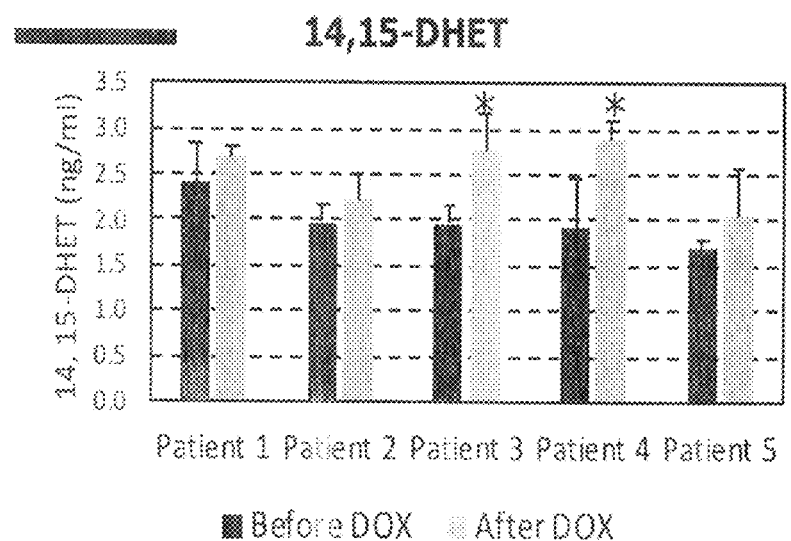
FIG. 4 shows the effect of doxorubicin (DOX) treatment on levels of a biologically active fatty acid in plasma samples obtained from breast cancer patients before and after 3 months of treatment with DOX. Plasma samples were extracted using ethyl acetate and levels of 14,15-DHET were assessed in triplicate for ELISA. Results expressed as mean±SD. *p<0.05.

A blind test for the early biomarker, 14,15-DHET (metabolite of sEH), was carried out with plasma samples from 5 breast cancer patients obtained before and after 3 months of DOX treatment (FIG. 4). No cardiotoxicity was detected in the patients at the time 3 months of DOX-treatment.

Fatty acids in the plasma samples (50 µl/sample) were extracted with ethyl acetate and levels of 14,15-DHET were assessed in triplicate samples using an ELISA kit from Detroit R&D.

Chemotherapy-associated cardiotoxicity is defined as either a cardiomyopathy with a reduction of left ventricular ejection fraction (LVEF) ≥5% to <55% with symptoms of heart failure or an asymptomatic reduction of LVEF ≥10% to <55% by the Cardiac Review and Evaluation Committee (CREC) (7).

The 14,15-DHET ELISA results showed that, although no cardiotoxicity was detected in any of the 5 patients after 3 months of DOX-treatment was completed, levels of 14,15-DHET significantly increased by ~38% and ~55% in plasma samples obtained from Patients #3 and #4, respectively ($p<0.05$) (FIG. 4).

According to our finding (FIG. 1 through FIG. 3), only Patients #3 and #4 were predicted to develop cardiotoxicity during recovery.

Indeed, only Patients #3 and #4 had reduction of LVEF higher than 20% (~28% and 22%, respectively) at 3 months after 3 months of DOX-treatment was completed (6 months including 3 months of treatment). Reduction of LVEF of Patients #3 and #4 remained around 20% at 6 months after 3 months of DOX-treatment was completed (9 months including 3 months of treatment).

Increased troponin I (TnI) levels which were found to be an early biomarker of anthracycline-dependent cardiotoxicity (5) were increased and decreased in plasma samples obtained from Patients #3 and #4, respectively, at 3 months after 3 months of DOX-treatment. TnI levels of Patients #1, #2 and #5 (no cardiotoxicity) were increased at 3 months after 3 months of DOX-treatment, which strongly suggested that additional early biomarkers are needed to compensate specificity of the TnI as an early cardiotoxicity biomarker.

Another shortcoming of the use of early cardiotoxicity biomarkers of heart muscle injury such as TnI is that a molecular inhibitor of the injury is difficult to produce. Contrary, inhibitors of sEH, which prevent conversion of a substrate of the enzyme to a metabolite, e.g., 14,15-EET to 14,15-DHET, are molecules which can inhibit the enzymatic activity by directly binding to the enzyme.

Honokiol (Sigma), a component of magnolia bark, and 12[[(tricycle[3.3.1.13,7]dec-1-ylamino)carbonyl]amino]-dodecanoic acid (AUDA) (Cayman), a synthetic sEH inhibitor, inhibited EET (1 µM)-dependent sEH activity in a reconstituted system with recombinant sEH and human kidney cells (ACHN). Both AUDA and honokiol were found to be potent inhibitors of the sEH activity.

sEH metabolites including 14,15-DHET are early serum biomarkers for prediction of cardiotoxicity. Early diagnosis of patients to predict cardiac dysfunction is necessary to adjust the anti-cancer drug treatment protocol. Moreover, inhibition of activity of the target enzyme, sEH, will ameliorate the chemotherapy-induced cardiotoxicity.

Figure 5B:
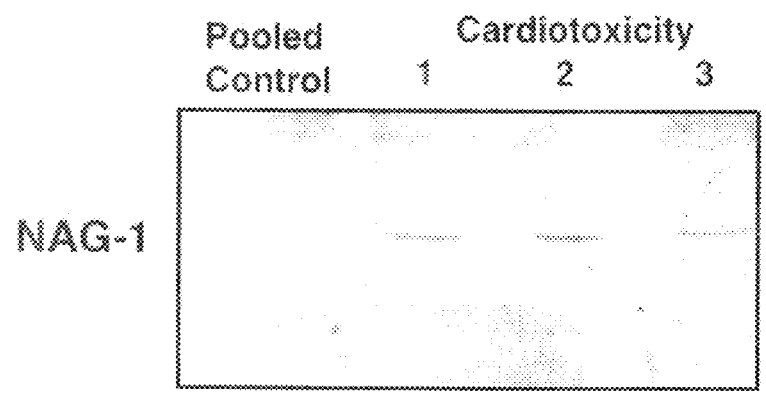

Expression of GDF-15 (NAG-1) was detected by Western blot analysis under non-reducing/non-denaturing condition using a Detroit R&D antibody to GDF-15. DGF-15 protein was up-regulated in plasma samples from 3 breast cancer patients with cardiovascular disease (cardiotoxicity) compared to pooled healthy subject plasma sample (Innovative Research) (FIG. 5). The result demonstrated that an increase in plasma GDF-15 level is a biomarker of cancer-therapy-induced cardiotoxicity.

Serum or plasma cardiotoxicity biomarkers cam be detected by ELISA, dot blot analysis and lateral flow (dipstick) immunoassay.

A facile label-free method using electrochemical microwell and nanowell biosensors which uses 1 µl blood or serum/plasma samples with or without dilution was developed to detect a change in current or impedance due to hybridization of a target molecule (biomarker) with a capture molecule (antibody).

Figure 6A:
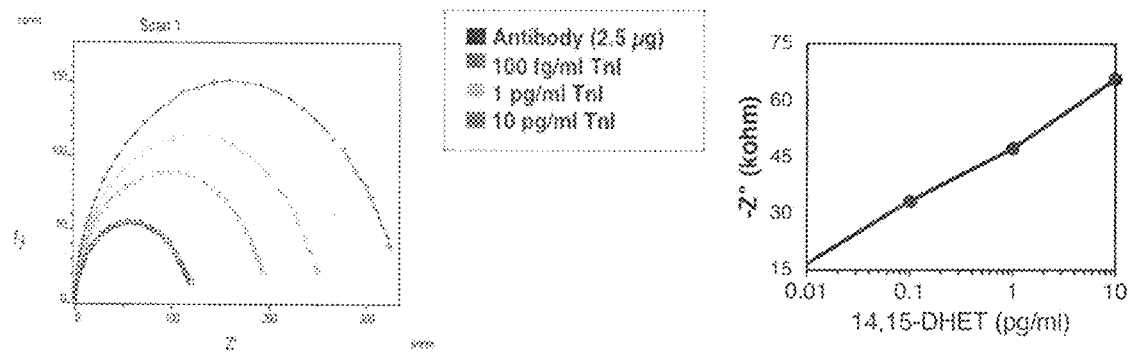
FIGS. 6A and 6B show quantitation of 14,15-DHET (A) and TnI (B) by standard curves using 8-channel nanowell electrodes. Various amounts of 14,15-DHET (A) or TnI (B) (100 fg/ml, 1 pg/ml and 10 pg/ml) were added to the channels coated with anti-14,15-DHET or TnI (Detroit R&D) and impedance was measured after dipping the electrode in ferro/ferricyanide (5 mM each), 100 mM KCl in PBS using an 8-channel Ivium potentio-n-stat (Ivium Technology). Impedance increased proportionally with increasing concentration of 14,15-DHET or TnI.
Figure 6B:
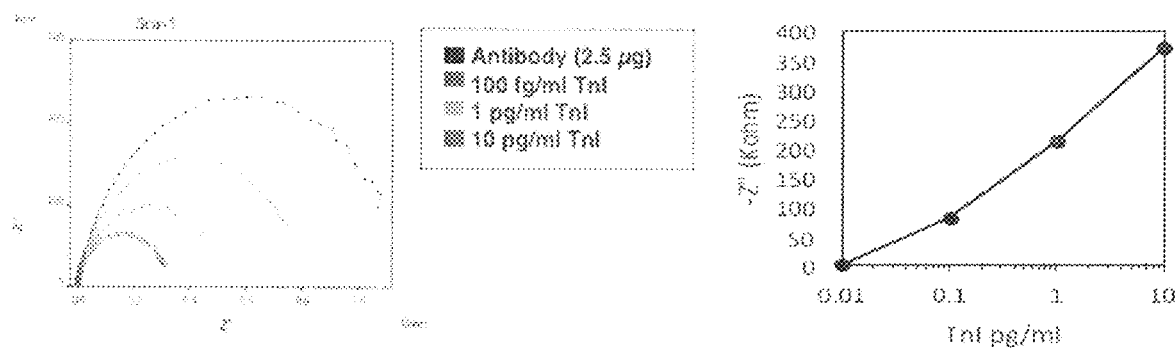

Hybridization of target fatty acids and proteins to the antibodies coated on microwell or nanowell surface was monitored using an Ivium Stat potentiometer (Ivium Technology). The impedance resulting from fatty acids and proteins binding to the nanogold surface was determined for redox conversion using ferri/ferrocyanide (5 mM each). Using Nyquist plots, the charge transfer resistance (Rct) increased as concentrations of biologically active fatty acids, 14,15-DHET (FIG. 6A), 20-HETE and 8-isoprostane, or TnI (FIG. 6B), increased. Limit of detection (LOD) for 14,15-DHET, 8-isoprostane, 20-HETE and TnI using nanowell technology was 100 fg/ml, which was 100-fold more sensitive compared with the LOD of STIP-1 target protein (10 µg/ml) (12), when an 8-channel electrode (700 µm$^2$ gold surface) containing 2,025×2,025 nanowells (Detroit R&D) was used.

Figures 7A, 7B, 7C:
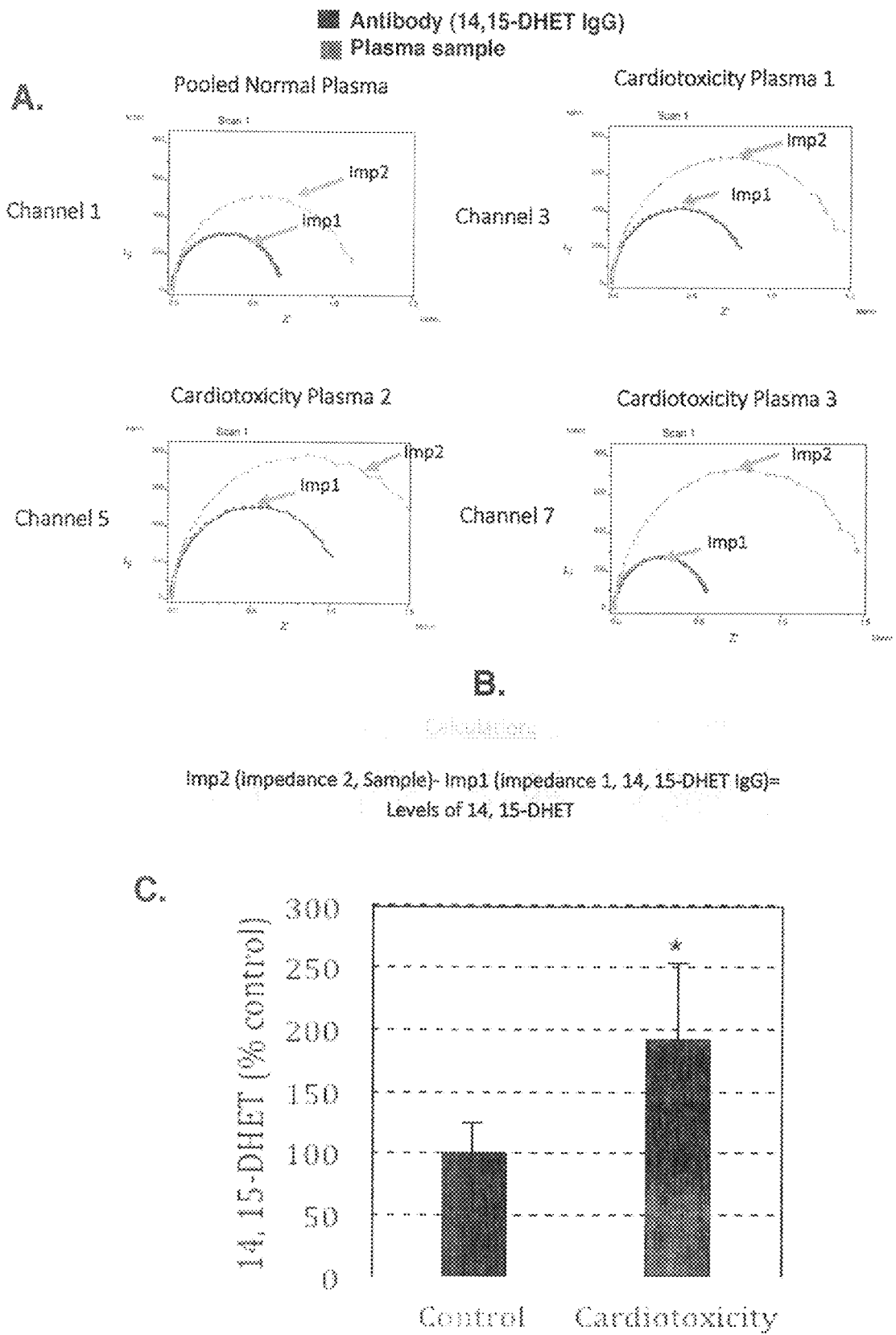
FIGS. 7A through 7C show changes in impedance after addition of plasma samples from pooled plasma from cancer-free women and 3 cardiomyopathy breast cancer patients (Innovative Research) measured by label-free electrochemical analyses using 90 nm nanowell electrodes conjugated with 14,15-DHET IgG (2.5 µg/ml). Impedance was measured after dipping the electrode in ferro/ferricyanide (5 mM each), 100 mM KCl in PBS using an 8-channel Ivium potentio-n-stat (Ivium Technology) (A). Formula for calculating 14,15-DHET (B). Percent of increase from control average was calculated and expressed as a mean±standard deviation (SD). *p<0.05 (C).

The 14,15-DHET levels in plasma samples from 3 breast cancer patients with cardiotoxicity were detected by nanowell technology and compared to a pooled plasma sample from non-cancer female donors (Innovative Research) (FIG. 7). Compared to the pooled control plasma sample, levels of 14,15-DHET increased in all 3 breast cancer patients with cardiotoxicity (FIG. 7A). The plasma 14,15-DHET level for each channel was calculated by subtracting the impedance level of 14,15-DHET IgG alone from the impedance level obtained with the sample added to the IgG-coated electrode (FIG. 7B). These results showed that levels of 14,15-DHET significantly ($p<0.04$) increased by ~90% in plasma samples obtained from breast cancer patients with cardiotoxicity compared to the control sample (FIG. 7C).

The plasma samples of Patient #4 (10-fold diluted) who developed DOX-dependent cardiotoxicity 3 and 6 months after completion of the 3 months DOX treatment were obtained before and after 3 months DOX treatment (FIG. 4). By 14,15-DHET nanowell label-free analysis, it was found that the 14,15-DHET level increased ~20-fold in the plasma sample obtained from Patient #4 after 3 months treatment with DOX compared to the plasma sample obtained before the treatment (n=4, $p<0.05$). The electrochemical result indicated that DOX treatment induced an increase in the level of 14,15-DHET which could be used to predict cardiotoxicity (early cardiotoxocity biomarker).

In addition, the fatty acid cardiotoxicity biomarkers, 14,15-DHET, 11,12-DHET and 8-isoprostane, can be isolated by affinity chromatography and gas or liquid chromatography to identify the fatty acids by mass spectrometry (MS). The protein cardiotoxicity biomarkers can be isolated by affinity chromatography or electrophoresis to identify the proteins by mass spectrometry (MS) or N-terminal sequencing or Western blot analysis.

The fatty acid and protein cardiotoxicity biomarkers can also be detected by other technologies including label-free nanotechnologies and dot blot and lateral flow immunoassays.

Interference RNA of mRNA of cardiotoxicity biomarkers including sEH, GDF-15, TnI and MPO can be used as anti-cardiotoxicity molecules in cells or animal disease models. They can also be used to treat patients.

Natural plant sEH inhibitors including honokiol-containing plants can be used to treat patients who have risk of sEH-dependent cardiotoxicity.

Some of the techniques used for screening of glycan, glycoprotein, glycan-binding protein and anti-antibody biomarkers in the present disclosure are practiced in the art, and most practitioners are familiar with the standard resource materials, which describe specific conditions and procedures. The methods used with and the utility of the present invention can be shown by the following non-limiting examples and accompanying figures.

EXAMPLES

Example 1

Biomarkers of Risk or Presence of Chemotherapy-Induced Cardiotoxicity Identified Using Rat H9c2 Cardiomyocyte Cells.

Rat H9c2 cell line was purchased from American Type Culture Collection (Manassas, Va.) and cultured on polystyrene culture plates in a humidified incubator at 37° C. in an atmosphere of 5% $CO_2$ and 95% air. The H9c2 cells were grown in high glucose DMEM supplemented with 4.5 g/l glucose, 0.15% sodium bicarbonate, 0.11% sodium pyruvate, 10% fetal bovine serum, 20 µM L-glutamine, 100 IU/ml penicillin and 10 µg/ml streptomycin. When cells reached 80-90% confluency, media was replaced with media containing 1 µM DOX (Sigma) dissolved in DMSO. Cells were treated for 2 hr and collected immediately (0 hr) or washed and kept for 2, 6 and 24 hr in media without DOX.

The effect of DOX on cell viability was determined by 3-[4,5-dimethylthiazol-2-yl]-2,5-diphenyltetrazolium bromide (MTT) assay (13). We found that the cells treated with 1 µM of DOX for 2 hr with medium replaced by fresh medium for another 24 hr maintained more than 90% cell viability.

For cell hypertrophy assay, rat H9c2 cells grown overnight in a plate containing a glass cover slip were fixed at 2, 6 and 24 hr after 2 hr 1 µM DOX treatment and stained with hematoxylin and eosin and images were taken using a using a Zeiss Axiovert microscope. ImageJ software was used to measure the surface area of the cells. After measurement of more than 100 cells per group, the results demonstrated increased cell surface area at 6 hr and 24 hr after DOX treatment. Importantly, no changes were observed in 2 hr (FIG. 2).

Our novel finding suggests that 2 hr after 2 hr of DOX treatment is the suitable time to measure a biomarker that can predict hypertrophy of cardiomyocytes at later time points, e.g., 6 hr or 24 hr, in vitro using H9c2 cells. Thus, based on this parameter (cell surface area), analysis of cell media at 2 hr (no damage) and 6 hr or 24 hr (heart damage) after 2 hr DOX treatment is a cell model to predict cellular damage in human patients occurring after completion of 3 months DOX treatment (no damage).

BNP mRNA was assessed in rat H9c2 cells. RNA (1 µg) was converted to cDNA using High Capacity cDNA Reverse Transcript Kit (Applied Biosystems). BNP were measured by real time PCR (Sybr green) using rat specific primers (13). Results were normalized using β-actin mRNA levels using a rat specific primer (13). Our results have shown that BNP levels were decreased 6 and 24 hr after 2 hr of DOX treatment (FIG. 1A) when cell hypertrophy was detected (FIG. 2).

The effect of DOX treatment induced an almost 4-fold increase of BNP mRNA at 2 hr of recovery after 2 hr DOX treatment (FIG. 1A) when changes in cell size was not observed (FIG. 2). This result confirms that increased BNP mRNA level is an early biomarker that precedes the incidence of cardiomyocyte hypertrophy.

sEH enzyme converts 14,15-EET to 14,15-DHET, so differential levels of 14,15-DHET will reflect sEH activity. After addition of 1 µM 14,15-EET to H9c2 cells, ~250 ng/ml 14,15-DHET was formed in cell media in 30 min and 4.5-fold higher level of 14,15-DHET was formed when the EET level was increased from 1 µM to 5 µM, verifying EET-dose-dependent 14,15-DHET formation by rat H9c2 cardiomyocyte cells.

Levels of 14,15-DHET in cardiomyocyte (H9c2 cell) media were assessed by the Detroit R&D 14,15-DHET ELISA. Media, 2 ml, was extracted with 2 ml acetyl acetate. and levels of 14,15-DHET increased after 2 hr, 6 hr and 24 hr following 2 hr DOX treatment (2 hr, 6 hr and 24 hr recovery) (FIG. 1B).

The effect of DOX treatment dramatically induced 14,15-DHET levels at 2 hr of recovery after 2 hr DOX treatment (FIG. 1B) when changes in cell size was not observed (FIG. 2). This result confirms that increased 14,15-DHET level is an early biomarker that precedes the incidence of cardiomyocyte hypertrophy.

Example 2

Identification of Biomarkers for Risk of Chemotherapy-Induced Cardiotoxicity Using Female Rats.

Early diagnosis followed by medical intervention is critical to prevent cardiotoxicity. Early DOX cardiotoxicity biomarkers are identified using rat H9c2 cardiomyocyte cells with and without 6 or 24 hr recovery period after DOX treatment (Example 1, FIG. 1 and FIG. 2). Heart tissue and serum samples from female rats after treatment with DOX for 2 weeks with and without a 2-week recovery period were obtained and increased levels of BNP mRNA in heart tissues and increased levels of 14,15-DHET in sera were detected after 2 week recovery, when cardiotoxicity was not detected, supporting our finding that BNP mRNA and 14,15-DHET (sEH metabolite) are early biomarkers of anthracycline-induced cardioxicity.

(DOX administration in laboratory animals has been performed to mimic human chemotherapy treatment and to analyze the secondary effect of DOX. Female Sprague-Dawley rats (Charles River, Ashland, Ohio) received two intravenous injections of either 3 mg/kg body weight (once a week for 2 weeks) of DOX (DOX-treated, n=12) or a similar volume of saline (Control, n=12). Because one of the outcomes of DOX treatment in animals is a reduced body weight gain, body weights for the rats were measured daily. After 2 weeks of recovery, the body weight or the weight gain of the control group (325±17) was ~20% higher than the DOX group (269±15 g).

Heart tissues were dehydrated, imbedded in paraffin and sliced. Slices were incubated in Mayer's hematoxylin reagent (ScyTek) for 5 min and covered with bluing reagent (ScyTek) for 15 seconds and eosin Y (ScyTek) solution for 3 minutes. Images of the rat cardiomyocyte were taken using a Zeiss Axiovert 200 microscope with RT Insight camera and SPOT Advanced Imaging software in 40× magnification at the Microscopy and Imaging Facility at Wayne State University.

Presence of vacuolization in heart tissue, a sign of cardiotoxicity (14), was not observed at 40× magnification. Thus, histological analyses suggest that the period of 2 weeks after DOX-injections using our rat-protocol is a time-period before the development of cardiotoxicity.

Rat specific primers for RT-PCR were purchase from IDT Integrated DNA technology (Table 1). Heart total RNA was extracted using the TRIzol method, cDNA was synthesized using High Capacity cDNA Reverse Transcript Kit (Applied Biosystems). Levels of mRNA in cardiomyocytes were measured by real time PCR (Sybr green) using rat specific primers. After 2 weeks recovery, levels of mRNA of both natriuretic peptides released from the atrium (ANP) (Table 1) and the ventricle (BNP) (Table 1, FIG. 3A) increased ~6- and 4-folds, respectively. Early increase of the BNP mRNA level without cell hypertrophy were confirmed using DOX-treated H9c2 rat cardiomyocytes (FIG. 1A). After 2 weeks recovery when no cardiac hypertrophy was detected, mRNA levels of myeloperoxidase (MPO) which plays a role in the inflammatory processes and s100 calcium-binding protein A9 (S100A9) increased and decreased, respectively, compared to mRNA levels of control rats (Table 1).

Biologically active fatty acids were extracted with ethyl acetate from 75 µl of serum samples (n=4) from control and DOX-treated animals with and without 2 weeks recovery. Levels of 14,15-DHET (sEH metabolite), 20-HETE (metabolite of cytochrome P450 4A/4F) and 8-isoprostane (non-enzymatic oxidative stress product) were measured using ELISA kits from Detroit R&D. The results demonstrated that all three biologically active fatty acids did not significantly change after two weeks (3 mg/kg body weight/week) of DOX treatment (no recovery). However, two weeks after the second injection (2 weeks recovery), when cardiotoxicity was still not detected, levels of 14,15-DHET (a metabolite of soluble epoxide hydrolase) and 8-isoprostane (non-enzymatic oxidative stress biomarker) were increased compared to the control group (FIG. 3B and FIG. 3D). No changes in levels of 20-HETE in rat serum samples between the two groups were observed (FIG. 3C). These results and rat cardiomyocyte study results demonstrated that increased 14,15-DHET and 8-isoprostane are early biomarkers to predict DOX-induced cardiotoxicity.

Example 3

Increased 14,15-DHET Level in Plasma Sample is an Early Biomarker which Predicts Cardiotoxicity (Decreased Heart Function) of Breast Cancer Patients.

Plasma samples from 5 breast cancer patients obtained before (n=5) and after (n=5) 3 months of DOX treatment (60 mg/m$^2$/injection for 4 injections). Among them, only the Patients #3 and #4 had reduction of LVEF higher than 20% at 3 and 6 months after 3 months of DOX-treatment was completed whereas no significant changes were observed with the other patients.

Biologically active fatty acids in the plasma samples (50 µl/sample) were extracted with ethyl acetate, dried and re-suspended with 30 µl of DMF followed by dilution buffer to 900 µl. Levels of 14,15-DHET were assessed in triplicate using an ELISA kit from Detroit R&D (100 µl/well). Results showed that levels of 14,15-DHET significantly increased (p<0.05) in plasma samples from Patients #3 and #4. In samples from Patients #2 and #5, the 14,15-DHET levels did not significantly increase (FIG. 4). By these results, Patients #3 and #4 are predicted to develop cardiotoxicity.

The results showed that 14,15-DHET is an early biomarker to predict a decrease in LVEF after DOX treatment. LVEF is a functional measurement used to verify the presence of abnormalities in the heart (cardiotoxicity) (1). Once the LVEF is decreased, it might be too late to recover to the normal LVEF by treatment. A challenge in this field is identification of an early biomarker that predicts such a change in the heart. Thus, early biomarkers which can predict chemotherapy-induced reduction of LVEF could allow patients to receive a therapy before cardiotoxicity occurs to prevent chemotherapy-induced-induced heart damage.

Example 4

Label-Free Microwell and Nanowell Technologies to Detect Biomarkers for Risk or Presence of Chemotherapy-Induced Cardiotoxicity.

The bare gold surface of the 8-channel 90 nm or 200 nm nanowell electrode (Detroit R&D) was coated with a self-assembly monolayer (SAM) by incubating the electrode with 10 mM of 11-mercaptoundecanoic acid (MUA) (Sigma) for 1 hr at room temperature and activated using 50 mM EDC and 50 mM NHS. The 14,15-DHET IgG (Detroit R&D) (FIG. 6A) or TnI IgG (Detroit R&D) (FIG. 6B) in PBS (2.5 µg/ml) was added to the EDC/NHS-activated electrode. The IgG level to obtain optimal results was experimentally obtained by using electrodes coated with various concentrations of IgG ranging 1 to 10 µg/ml.

Label-free 8-isoprostane nanowell analysis with 5 µg/ml and 10 µg/ml IgG 8-isoprostane IgG revealed that analysis with the nanowell electrode coated with 5 µg/ml was better than the 10 µg/ml IgG-coated electrode for a standard curve production (LOD, 100 fg/ml).

Various amounts of 14,15-DHET or TnI protein (100 fg/ml, 1 pg/ml and 10 pg/ml) were added to the channels. Cyclic voltammetry (CV) was measured after dipping the electrode in ferro/ferricyanide (5 mM each), 100 mM KCl in PBS using an Ivium potentio-n-stat potentiometer (Ivium Technology). Impedance increased proportionally with increasing concentration of 14,15-DHET or TnI added to the electrode (FIG. 6). Low variance of impedance values among the channels was observed when 2.5 µg/ml of IgG was used. The LOD values of both 14,15-DHET and TnI by the label-free technology were 100 fg/ml (FIG. 6).

The 14,15-DHET 90 nm nanowell analysis was carried out using pooled female control plasma sample and plasma samples from 3 breast cancer patients with cardiotoxicity (~1 µl/channel) (Innovative Research) (FIG. 7A). Changes in impedance after addition of the pooled normal plasma and 3 cardiotoxicity plasma samples were measured by label-free electrochemical analyses using 90 nm nanowell electrodes conjugated with 14,15-DHET IgG (2.5 µg/ml). Impedance was measured after dipping the electrode in ferro/ferricyanide (5 mM each), 100 mM KCl in PBS using an 8-channel Ivium potentio-n-stat (Ivium Technology) (FIG. 7A). The formula for calculating 14,15-DHET is shown (FIG. 7B). Percent increases over the an average control value was calculated and expressed as a mean±standard deviation (SD). *p<0.05 (FIG. 7C).

Compared to the pooled control sample, levels of 14,15-DHET of all 3 breast cancer patients with cardiotoxicity increased (FIG. 7A). The plasma 14,15-DHET level for each channel was calculated by subtracting the impedance level of IgG alone from the impedance level obtained with the sample added to the IgG-coated electrode (FIG. 7B). Percent increases from an average of controls showed a significant difference between the control and cardiotoxicity groups (FIG. 7C). These results suggest that 2.5 µg/ml 14,15-DHET IgG is the ideal concentration for measurements of plasma 14,15-DHET levels and that levels of 14,15-DHET significantly (p<0.04) increased ~90% in plasma samples obtained from breast cancer patients with cardiotoxicity.

TABLE 1

Biomarker candidates to predict cardiotoxicity in rats after DOX injection. Sample was collected at ~48 hr after 2 weeks DOX injection (3 mg/kg body weight/week) (no recovery) and at 2 weeks after the last injection of DOX (2 weeks recovery). Results were assessed by ELISA and by real-time (RT)-PCR. Heart tissue biomarkers were normalized by the β-actin mRNA level.

| | Biomarker | Method | 2 weeks DOX Treatment (No Recovery) | 2-Weeks after 2 Weeks DOX Treatment (2 Weeks Recovery) |
|---|---|---|---|---|
| Serum Biomarker | 14,15-DHET | ELISA | No change | ↑ 3.5-fold |
| | 20-HETE | ELISA | No change | No change |
| | 8-Isoprostane | ELISA | No change | ↑ 3-fold |
| Heart Tissue Biomarker | ANP | RT-PCR | ↓ 2-fold | ↑ 5-fold |
| | BNP | RT-PCR | No change | ↑ 4-fold |
| | MPO | RT-PCR | No change | ↑ 2-fold |
| | S100A9 | RT-PCR | No change | ↓ 2.5-fold |

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

REFERENCES

1. CDC, the National Center for Health Statistics (NCHS): Underlying cause of death 1999-2013 on CDC WONDER Online Database. Data are from the Multiple Cause of Death Files, 1999-2013, as compiled from data provided by the 57 vital statistics jurisdictions through the Vital Statistics Cooperative Program. Accessed Feb. 3, 2015.
2. Fryar C D, Chen T, Li X. Prevalence of uncontrolled risk factors for cardiovascular diseases: United States, 1999-2010. NCHS Data Brief. 2012 103:1-8.
3. Lotrionte M, Biondi-Zoccai G, Abbate A, Lanzetta G, D'Ascenzo F, Malavasi V, Peruzzi M, Frati G, Palazzoni G. Review and meta-analysis of incidence and clinical predictors of anthracycline cardiotoxicity. Am J Cardiol 2013 112:1980-4.
4. http://www.breastcancer.org/symptoms/understand_bc/statistics.
5. Ky B, Putt M, Sawaya H, French B, Januzzi J L, Sebag I A, Plana J C, Cohen V, Banchs J, Carver J R, Wiegers S E, Martin R P, Picard M H, Gersten R E, Halpern E F, Passeri J, Kuter I, Scherrer-Crosbie M. Early increases in multiple biomarkers predict subsequent cardiotoxicity in patients with breast cancer treated with doxorubicin, taxanes, and trastuzumab. J Am Coll Cardiol. 2014 8:809-16
6. Stevens P L, Lenihan D J. Cardiotoxicity due to Chemotherapy: The Role of Biomarkers. Curr Cardiol Rep. 2015 17:49.
7. Seidman A, Hudis C, Pierri M K, Shak S, Paton V, Ashby M, Murphy M, Stewart S J, Keefe D. Cardiac dysfunction in the trastuzumab clinical trials experience. J Clin Oncol. 2002 5:1215-21.
8. Kim H, Capdevile J H, Novak R R, Kroetz D. U.S. Pat. No. 6,534,282, B2. 2003. http://www.freepatentsonline.com/6534282.pdf.
9. Yang T, Peng R, Guo Y, Shen L, Zhao S, Xu D. The role of 14,15-dihydroxyeicosatrienoic acid levels in inflammation and its relationship to lipoproteins. Lipids Health Dis. 2013 23:151.
10. Santos J M, Park J A, Joiakim A, Putt D A, Taylor R N, Kim H. The role of soluble epoxide hydrolase in preeclampsia. Med Hypotheses. 2017 October; 108:81-85.
11. Cha M S, Lee J K, Cho S H, Park J G, Lee H Y, Lim S H, Yoon Y R. Quantitative analysis of H5N1 DNA hybridization on nanowell array electrode. J Nanosci Nanotechnol 2013 13:5245-9.
12. Lee J, Cho S, Lee J, Ryu H, Park J, Lim S, Oh B, Lee C, Huang W, Busnaina A, Lee H. Wafer-scale nanowell array patterning based electrochemical impedimetric immunosensor. J Biotechnol. 2013 168:584-8.
13. Zordoky B N, Anwar-Mohamed A, Aboutabl M E, El-Kadi A O. Acute doxorubicin cardiotoxicity alters cardiac cytochrome P450 expression and arachidonic acid metabolism in rats. Toxicol Appl Pharmacol. 2010 242: 38-46.
14. Reagan W J, York M, Berridge B, Schultze E, Walker D, Pettit S. Comparison of cardiac troponin I and T, including the evaluation of an ultrasensitive assay, as indicators of doxorubicin-induced cardiotoxicity. Toxicol Pathol. 2013; 41(8):1146-58.

The invention claimed is:

1. A method to identify risk of chemotherapy-induced cardiotoxicity with reduction of left ventricular ejection fraction (LVEF) higher than 20% at 3 to 6 months after DOX-treatment was completed compared with LVEF assessed before DOX treatment for a breast cancer patient who has been treated with a cumulative doxorubicin (DOX) dose of 240 mg/m$^2$ using 14,15-dihydroxyeicosatrienoic acid (14,15-DHET) that predicts cardiotoxicity by the steps of:
   obtaining a baseline blood sample from a breast cancer patient prior to treatment with a cumulative DOX dose of 240 mg/m$^2$;
   obtaining a blood sample from the breast cancer patient after completion of treatment with a cumulative DOX dose of 240 mg/m$^2$;
   determining levels of 14,15-DHET in blood samples obtained before and after DOX treatment;
   identifying the patient with the increased level of 14,15-DHET at 38% and higher in the blood sample obtained after the treatment compared to the blood sample obtained before the treatment and
   identifying the patient with risk of chemotherapy-induced cardiotoxicity.

2. The method of claim 1, wherein 14,15-DHET is determined by ELISA.

3. A method to identify a breast cancer patient with soluble epoxide hydrolase (sEH) dependent cardiotoxicity with reduction of LVEF higher than 20% at 3 to 6 months after DOX-treatment compared with LVEF assessed before DOX treatment by measuring 14,15-DHET by the steps of:
   identifying a breast cancer patient with cardiotoxicity with reduction of LVEF higher than 20% at 3 to 6 months after DOX-treatment compared with LVEF assessed before DOX treatment with a cumulative DOX dose of 240 mg/m$^2$;
   determining the 14,15-DHET level in blood of the patient with cardiotoxicity;
   determining the 14,15-DHET level of a control blood sample of the patient obtained before treatment;
   identifying the patient whose 14,15-DHET level increased 38% and higher compared to the control blood sample and
   confirming the patient as a patient with sEH-dependent cardiotoxicity.

4. The method of claim 3, wherein 14,15-DHET is determined by ELISA.

* * * * *